US00PP15440P3

(12) United States Plant Patent
Jonkers

(10) Patent No.: US PP15,440 P3
(45) Date of Patent: Dec. 21, 2004

(54) *IMPATIENS* PLANT NAMED 'DIDI APPLEBLOSSOM'

(50) Latin Name: *Impatiens walleriana*
Varietal Denomination: Didi Appleblossom

(75) Inventor: Johanna B. Jonkers, Hoorn (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/397,994

(22) Filed: Mar. 25, 2003

(65) Prior Publication Data

US 2004/0194182 P1 Sep. 30, 2004

(51) Int. Cl.[7] ..... A01H 5/00

(52) U.S. Cl. ..... Plt./317

(58) Field of Search ..... Plt./317

(56) References Cited

PUBLICATIONS

UPOV–ROM GTITM, Plant Variety Database, 2003/06, GTI Jouve Retrieval Software, Citation for *Impatiens* Didi Appleblossom.*

* cited by examiner

*Primary Examiner*—Anne Marie Grunberg
*Assistant Examiner*—June Hwu
(74) *Attorney, Agent, or Firm*—Jondle & Associates P.C.

(57) ABSTRACT

An *Impatiens* cultivar particularly distinguished by soft-pink colored flowers, compact habit and good basal branching.

1 Drawing Sheet

Genus and species: *Impatiens walleriana.*
Variety denomination: 'Didi Appleblossom'.

BACKGROUND OF THE NEW PLANT

The present invention comprises a new and distinct cultivar of *Impatiens*, botanically known as *Impatiens walleriana,* and hereinafter referred to by the cultivar name 'Didi Appleblossom'. The new cultivar is asexually reproduced from vegetative cuttings and tissue culture resulting from the cross of the seed/pod parent IDT-32-49, a white proprietary line that is unnamed and unpatented×IN-1787-7, a light salmon-rose proprietary line that is unnamed and unpatented.

'Didi Appleblossom' is a product of a planned breeding program intended to create new impatiens plants with soft pink colored flowers, compact habit, good basal branching and moderately vigorous growth.

The new cultivar was created in 2000 in Andijk, The Netherlands and has been asexually reproduced repeatedly by vegetative cuttings and tissue culture in Gilroy, Calif., Andijk, The Netherlands and Guatemala over a two and half year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new *Impatiens* plant is illustrated by the accompanying photograph which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Didi Appleblossom'. The data which defines these characteristics were collected from asexual reproductions carried out in Gilroy, Calif. The plant history was taken on 6 month old plants grown in 6-inch pots, in a poly-covered greenhouse under natural light and color readings were taken in the greenhouse. Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.—Impatiens walleriana.*
*Commercial.—Impatiens.*

Form: Compact, small mounded.

Growth and branching habit: Compact habit, good basal branching, moderately vigorous, pinching of the terminal apices enhances branching.

Height: From soil level to top of blooms: Approximately 10–20 cm.

Width: Approximately 30–40 cm including flowers.

Time to produce a finished flowering plant: 8–10 weeks for a 4-inch pot.

Outdoor plant performance: Shade, intermediate flowering, free-flowering all year, some heat tolerance. Use in hanging baskets, mixed containers, window boxes and mass plantings.

Time to initiate and develop roots: Approximately 10–21 days in the greenhouse.

Root description: Fibrous, fleshy, white.

THE LEAVES

Arrangement: Alternate.
Length: 4.0–6.0 cm.
Width: 2.9–3.2 cm.
Leaf blade shape: Ovate.
Leaf margin: Crenate with ciliate (1) between each lobe.
Apex aspect: Cuspidate with one ciliate at the tip.
Base aspect: Acuminate.
Foliage color: Upper side, RHS 147A (yellow-green); Underside, RHS 147B (yellow-green) with 137C (green) veining.
Texture: Galbrous.
Venation: Pinnate.
Venation color: RHS 145C (green), fading into the leaf until almost disappearing.
Petiole length: 1.0–1.3 cm.
Petiole diameter: 0.25–0.3 cm.
Petiole color: RHS 145C (green).
Petiole texture: Glabrous.

THE STEM

Length: 20–25 cm.
Diameter: 0.3–0.5 cm.
Internode length: 0.1–1.4 cm.
Color: Between RHS 144A and B (yellow-green).
Texture: Glabrous.
Stem anthocyanin: No.
Pedicel diameter: 0.15 cm.
Pedicel length: 2.1–2.4 cm.
Pedicel color: RHS 144C (yellow-green).
Pedicel texture: Glabrous.
Peduncle length: 1.9–2.1 cm.
Peduncle diameter: 0.2 cm.
Peduncle color: RHS 144C (yellow-green).
Peduncle texture: Glabrous.

THE BUD

Shape: Ovate.
Diameter: 0.8–1.2 cm.
Length: 1.0–1.5 cm.
Color at tight bud: RHS 62D (red-purple) with prominent RHS 144A (yellow-green) keel down the topside.

THE FLOWER

Blooming habit: Free-blooming throughout the growing season.
Inflorescence type: Racemes in leaf axis.
Number of flowers per raceme and/or whorl: 11–20 including buds.
Number of petals per flower: 15–20.
Floret form: Fully double, rosette forming.
Flower color: Upper side, dorsal petal RHS 69D (red-purple); lateral petals RHS 69D (red-purple) with RHS 69A (red-purple) inner petals.
Flower color: Underside, dorsal is RHS 69D (red-purple) with a keel RHS 144A (yellow-green); lateral RHS 69D (red-purple).
Floret diameter: 3.6–4.0 cm.
Petal size, dorsal: Length 1.8–1.9 cm; width 2.5–2.7 cm; shape orbicular; apex shape retuse-emarginate. Lateral petal size: length 2.0–2.2 cm; width 1.6–1.7 cm; shape obovate; apex shape retuse-emarginate.
Petal base shape: Fused.
Petal margin: Entire.
Petal texture: Papillose.
Sepals: Three, one larger than the others with a spur.
Large sepal: Color semi translucent white with a RHS 143C (green) tip of approximately 0.1 cm; length 1.2–1.4 cm; width 0.9–1.0 cm; shape ovate; apex shape cuspidate; base shape fused.
Spur color: RHS 144C (yellow-green) with RHS 144A (yellow-green) tip of 0.1 cm in length; length 3.2–3.4 cm.
Small sepal: Color is RHS 144A (yellow-green); length 0.3 cm; width 0.1 cm; shape ovate; apex shape acute; base shape fused.
Sepal texture: Glabrous.
Lastingness of individual blooms: 4–8 days.
Fragrance: None.

THE REPRODUCTIVE ORGANS

There are no reproductive organs on these flowers. Stamens and pistils are transformed into flower leaves.

DISEASE AND INSECT RESISTANCE

Not observed.

COMPARISON WITH KNOWN CULTIVARS

'Didi Appleblossom' differs from the female parent in the following ways. The female is a white and single flowered while the 'Didi Appleblossom' is a soft pink and double flowered.

'Didi Appleblossom' differs from the male parent in the following ways. The male is a light salmon-rose and single flowered while the 'Didi Appleblossom' is a soft pink and double flowered. 'Didi Appleblossom' also has more compact habit than the male.

I claim:

1. A new and distinct cultivar of *Impatiens* plant as shown and described herein.

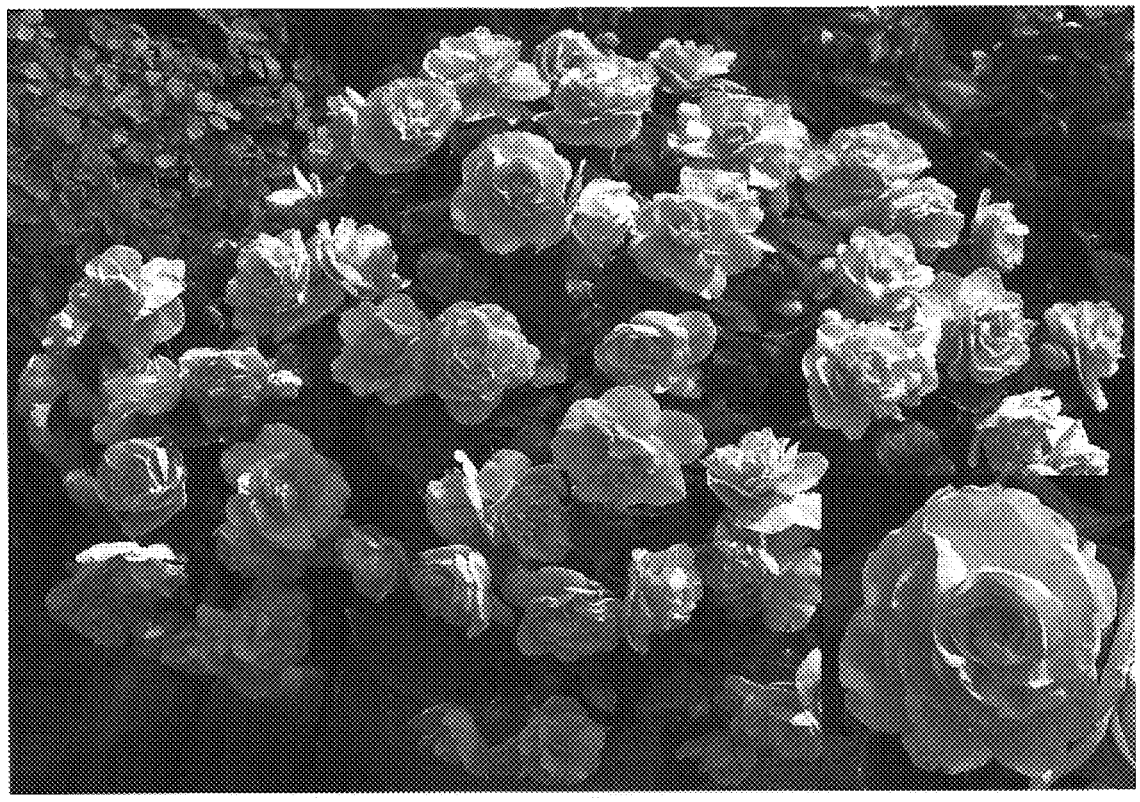

* * * * *